US00PP14138P39

(12) United States Plant Patent
Greenwood

(10) Patent No.: US PP14,138 P3
(45) Date of Patent: Sep. 16, 2003

(54) HYBRID TEA ROSE PLANT NAMED 'WEKCHRISG'

(75) Inventor: Christopher W. Greenwood, Glendora, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 09/981,227

(22) Filed: Oct. 15, 2001

(65) Prior Publication Data

US 2003/0074701 P1 Apr. 17, 2003

(51) Int. Cl.[7] ..... A01H 5/00

(52) U.S. Cl. ..... Plt./138

(58) Field of Search ..... Plt./130, 131, 138

*Primary Examiner*—Howard J. Locker

(74) *Attorney, Agent, or Firm*—Christie, Parker & Hale, LLP

(57) ABSTRACT

A new variety of Hybrid Tea rose suitable for garden decoration, having flowers of Cerise Pink with lighter reverse petal coloration.

1 Drawing Sheet

BACKGROUND OF THE INVENTION

This invention relates to a new and distinct variety of Hybrid Tea Rose. The varietal denomination of the new variety is 'WEKchrisg'. It was discovered in the summer of 1995 in Glendora, Calif. as a branch mutation of unknown origin of the cultivar 'WEKjoe' (U.S. Plant Pat. No. 9,389).

SUMMARY OF THE INVENTION

Among the features which distinguish the new variety from other presently available and commercial rose cultivars known to the inventor are the following combination of characteristics: its very large foliage, its flowers of cerise pink coloration, its vigorous very tall growing habit and its extremely long stems. The plant has an upright growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagation. 'WEKchrisg' may be asexually propagated by cuttings, budding on the rootstock of 'Dr. Huey' and grafting.

COMPARISON WITH PARENT

The new rose may be distinguished from its parent, 'WEKjoe' by the following combination of characteristics: whereas 'WEKchrisg' bears flowers of cerise pink coloration with a lighter reverse, 'WEkjoe' bears flowers of white coloration edged with pink.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Royal Horticultural Society Colour Chart (1966) and terminology used in the color descriptions herein refers to plate numbers in this color chart except where common terms of color definition are employed.

DESCRIPTION OF THE NEW VARIETY

The following description is of 3 to 4 year-old rose plants of the new variety grown outdoors in Upland, Calif. in the month of August. Phenotypic expression may vary with environmental, cultural and climatic conditions, as well as differences in conditions of light and soil.

FLOWER

The new variety usually bears its flowers singly, sometimes in clusters of 2 to 3 or more per stem. Flowers are borne in somewhat regular flat to rounded clusters on very strong long stems (about 50 to 122 cm). Outdoors, the plant blooms abundantly and nearly continuously during the growing season. The flowers have a slight tea fragrance.

BUD

The peduncle is about 5.3 to 8.2 cm in length, of somewhat heavy caliper (about 0.3 to 0.5 cm in diameter), and usually erect. It is moderately smooth, with many stipitate glands and some hairs. Peduncle color is between 144A and 147C sometimes very lightly suffused, especially on the side exposed to the sun, with between 183D and 187C.

Before the calyx breaks, the bud is about 1.8 to 2.6 cm in diameter at the widest point, about 2.9 to 3.8 cm in length, and pointed to somewhat ovoid in shape.

The surface of the bud bears some stipitate glands and some slender foliaceous appendages, usually with slender entire to slightly serrate foliaceous parts extending beyond the tip of the bud about ¼ or more of its length.

Bud color is between 144A and 147C sometimes very lightly suffused, especially on the side exposed to the sun, with between 183D and 187C.

The sepals are about 3.2 to 3.9 cm in length and about 0.8 to 1.2 cm in width at the widest point. The outer surface of the sepal is between 144A and 147C sometimes very lightly suffused especially on the side exposed to the sun, with between 183D and 187C. The sepals on the mature hips are fugacious.

The inner surface of the sepal is between 143C and 139D, covered with fine wooly tomentum; sepal margins are lined with few stipitate glands and hairs.

As the petals open (after the calyx breaks), the bud is pointed to somewhat ovoid in form, about 2.2 to 3.3 cm in diameter at the widest point and about 3.3 to 4.5 cm in length.

On the under surface of the newly opened petals, at the point where the petal attaches, there is a moderately large zone of between 4D and 8D that gradually suffuses to as dark as between 54A and 59C at the very edge of the petal.

The color of the upper surfaces of the newly opened petals is between 58B and 59B. At the point where the petal attaches, there is a moderately large zone of between 4D and 8D.

BLOOM

When fully open, the bloom ranges from about 9.5 to 13.2 cm in diameter. Petalage is double with about 25 to 30 petals and about 1 to 3 petaloids irregularly arranged. When partially open, the bloom form is somewhat cupped to high centered, and the petals are moderately spiraled to somewhat cupped with petal edges somewhat reflexed outward. When fully open, the bloom form is more cupped to somewhat flat, and the petals are more loosely cupped to slightly undulated with petal edges moderately reflexed outward.

PETALS

The substance of the petals is moderately heavy to leathery and of medium thickness, with upper surfaces moderately satiny and under surfaces slightly shiny to somewhat matte.

The outer petals are nearly round to broadly obovate in shape with rounded apices. The inner petals are more obovate to somewhat ovate in shape with rounded apices. The petals are about 4.5 to 5.1 cm in length and about 4.2 to 5.8 cm in width at the widest point. Petal margins are entire.

NEWLY OPENED FLOWER

The under surface of the outer, intermediate and inner petals is between 64D and 73B. At the point where the petal attaches, there is a medium sized zone of between 4D and 2D. The upper surface of the outer, intermediate and inner petals is between 61C and 68B. At the point where the petal attaches, there is a moderately large zone of between 2D and 1D.

The general tonality of the newly opened flower is between 61C and 68B.

THREE-DAY-OLD FLOWER

The under surface of the outer and inner petals is between 68D and 73C. At the point where the petal attaches, there is a somewhat large zone of between 155B and 2D. The upper surface of the outer and inner petals is between 68C and 73C. At the point where the petal attaches, there is a moderately large zone of between 155B and 2D.

The general tonality of the three-day-old flower is between 68C and 73C.

On the spent bloom, the petals usually drop off cleanly.

In August in Upland, Calif., blooms on the bush growing outdoors generally last about 4 to 5 or more days. Cut roses from plants grown outdoors and kept at normal indoor living temperatures generally last about 4 to 5 or more days.

MALE REPRODUCTIVE ORGANS

Stamens are average in number (average about 105) and are arranged regularly about the pistils; a few are mixed with petaloids.

The filaments are of medium length (about 0.4 to 1.1 cm), most with anthers. Some filaments are near 46A whereas others are near 2C at the base suffusing to near 8C near the top.

The anthers are medium for the class and all open approximately at the same time. Anther color is between 23C and 21C when immature and near 164C at maturity.

Pollen is abundant.

FEMALE REPRODUCTIVE ORGANS

Pistils vary in number (average about 120). The styles are somewhat uneven and loosely bunched.

Stigma color is near 13C. Style color is between 1C and 3D at the base suffusing to near 46C near the top.

Ovaries are usually all enclosed in the calyx.

Hips are globular in form and near 21C in color when ripe. The hip surface is very smooth with thick fleshy walls.

The seeds are irregularly rounded, smooth in texture, approximately 18 to about 26 per hip, about 0.4 to 0.7 cm in diameter at the widest point and between 165B and 165C in color.

FOLIAGE

The compound leaves are usually comprised of 3 to 5 or more leaflets and are borne very abundantly. The 5-leaflet leaves are about 14.6 to 18.8 cm in length and about 14.3 to 16.5 cm in width at the widest point, leathery in texture, and semi-glossy in finish. The terminal leaflets are about 6.7 to 10.9 cm in length and about 4.3 to 6.0 cm in width at the widest point, shaped ovate to somewhat oval with moderately acute apices and moderately rounded to somewhat acute bases. Their margins are usually simply serrate.

The upper surface of the mature leaf is between 137A and 147A. The under surface of the mature leaf is between 138B and 147C.

The upper surface of the young leaf is between 143C and 147C, sometimes heavily suffused with between 183A and 187B. The under surface of the young leaf is between 144B and 143D, usually heavily suffused with between 183A and 187B.

The rachis is somewhat heavy in caliper and moderately rough. The upper side is lightly grooved with few hairs and some stipitate glands on the edges of the grooves. The under side of the rachis is moderately rough with few stipitate glands and some small prickles. The rachis color is between 144C and 146D.

The stipules are about 1.2 to 1.6 cm in length, of moderately narrow width (about 0.4 to 0.7 cm) with somewhat short straight points that usually turn out at an angle of less than 90 degrees. The color of the stipules is between 144C and 146D.

The petiole is about 1.1 to 2.0 cm in length and about 0.2 to 0.3 cm in diameter at the widest point. The petiole color is between 144C and 146D.

The plant displays an average degree of resistance to powdery mildew and rust as compared to other commercial varieties grown under comparable conditions in Upland, Calif.

To best information and belief through systematic observations as indicated by USDA Plant Hardiness Zone Map, the plant's winter hardiness is between zone 5b and 6a. The plant's drought/heat tolerance is not known.

GROWTH

The plant has a very tall very upright growing habit (about 220 to 280 cm in height and about 120 to 140 cm spread at the widest point), with full branching. It displays very vigorous growth and the canes are of moderately heavy caliper for the class.

The color of the major stems is between 144B and 146C. They bear some large prickles that are about 0.4 to 0.8 cm in length.

The large prickles are moderately angled downward with a medium length moderately broad oval base; prickle color is between 164A and 165B. The major stem bears no small prickles.

The color of the branches is between 144A and 138B. They bear many large prickles which are of similar size and shape to the large prickles on the major stems; prickle color is between 151A and 160A. The branches bear some small prickles of similar shape and coloration.

The color of the new shoots is between 143C and 148B often lightly suffused with between 183C and 187D. They bear many large prickles which are of similar size and shape to the large prickles on the major stems; prickle color is near 184C. The shoots bear some small prickles of similar shape and coloration.

I claim:

1. A new and distinct Hybrid Tea rose plant of the variety substantially as described and illustrated herein.

* * * * *

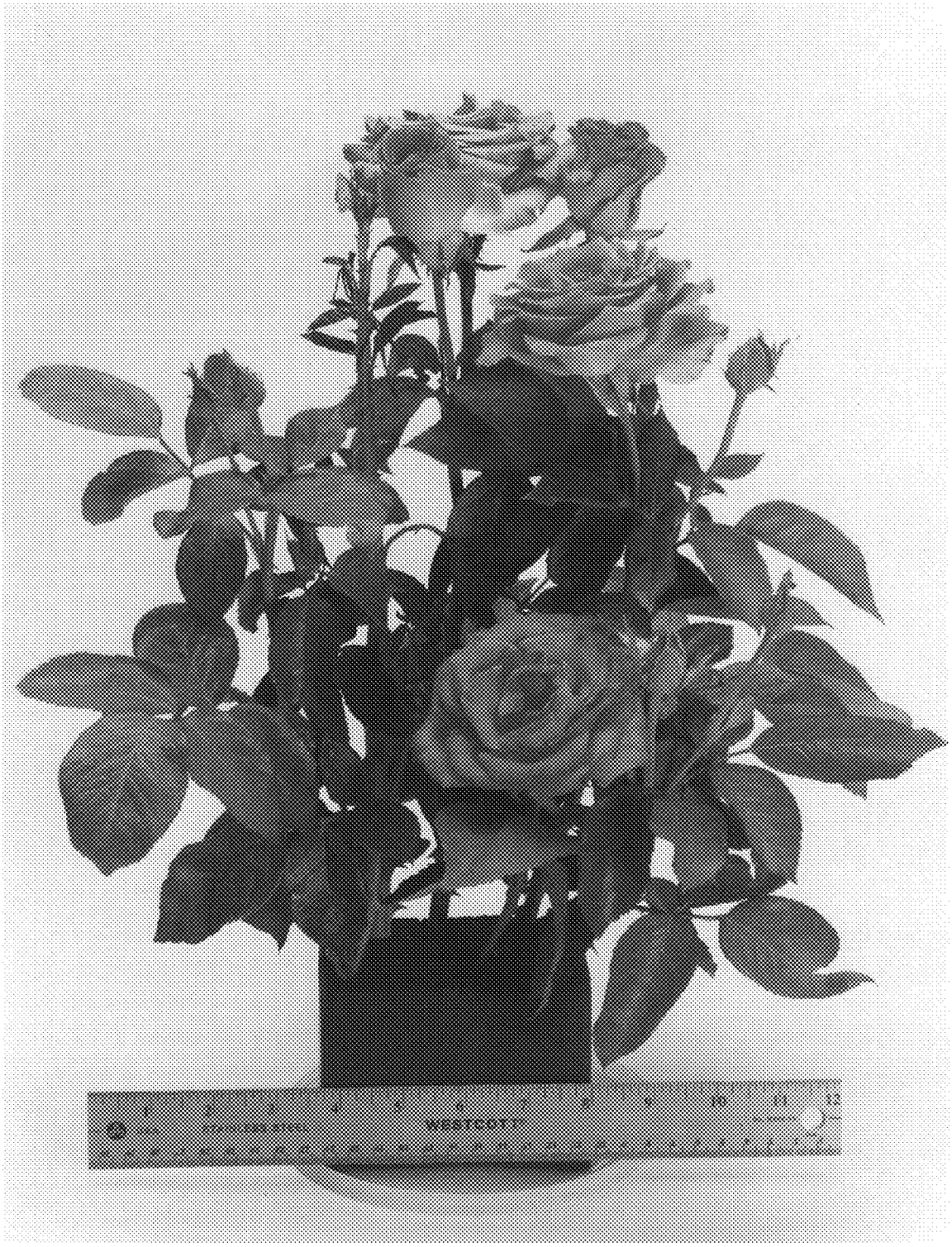
WESTCOTT